US 10,780,391 B2
Sep. 22, 2020

(12) United States Patent
Prasad et al.

(10) Patent No.: US 10,780,391 B2
(45) Date of Patent: Sep. 22, 2020

(54) INTEGRATED BIOGAS CLEANING SYSTEM TO REMOVE WATER, SILOXANES, SULFUR, OXYGEN, CHLORIDES AND VOLATILE ORGANIC COMPOUNDS

(71) Applicants: Alakh Prasad, Vancouver (CA); Kevin Marchand, Vancouver (CA)

(72) Inventors: Alakh Prasad, Vancouver (CA); Kevin Marchand, Vancouver (CA)

(73) Assignee: Quadrogen Power Systems, Inc., Vancouver (CA)

( * ) Notice: Subject to any disclaimer, the term of this patent is extended or adjusted under 35 U.S.C. 154(b) by 188 days.

(21) Appl. No.: 15/945,627

(22) Filed: Apr. 4, 2018

(65) Prior Publication Data

US 2018/0221817 A1 Aug. 9, 2018

Related U.S. Application Data

(63) Continuation of application No. 13/810,197, filed as application No. PCT/CA2011/000825 on Jul. 15, 2011, now abandoned.

(30) Foreign Application Priority Data

Jul. 15, 2010 (CA) .................................. 2709722

(51) Int. Cl.
    *B01D 53/75* (2006.01)
    *C01B 7/07* (2006.01)
    (Continued)

(52) U.S. Cl.
    CPC ............... *B01D 53/75* (2013.01); *C01B 7/07* (2013.01); *C01B 17/16* (2013.01); *C01B 17/164* (2013.01);
    (Continued)

(58) Field of Classification Search
    None
    See application file for complete search history.

(56) References Cited

U.S. PATENT DOCUMENTS

| 4,181,503 A | 1/1980 | Lesieur et al. |
| 4,374,654 A | 2/1983 | McCoy |

(Continued)

FOREIGN PATENT DOCUMENTS

| CA | 2474055 A1 | 7/2003 |
| JP | S58215488 A | 12/1983 |

(Continued)

OTHER PUBLICATIONS

Office Action dated Feb. 22, 2019 in connection with Korean patent application No. 10-2013-7003784.

(Continued)

*Primary Examiner* — Anita Nassiri-Motlagh
(74) *Attorney, Agent, or Firm* — Cook Alex, Ltd.; Ryan M. Truesdale

(57) ABSTRACT

A biogas cleaning method for purifying a biogas waste stream to form a combustible clean biofuel uses a biogas cleaning system that includes a gas control system, a deoxidizer catalyst bed, a hydrosulfurization catalyst bed, a hydrogen sulfide adsorption bed and a thermal sensor controller. The biogas cleaning method includes using a biogas source to introduce a biogas waste stream into the biogas cleaning system, blending hydrogen with the biogas waste stream, combusting the blended hydrogen and biogas waste stream to remove oxygen, hydrogenating the heated biogas waste stream to convert sulfur species to hydrogen sulfide and adsorbing the hydrogen sulfide from the biogas stream. In some embodiments, a biogas cleaning system also includes a sulfur polisher adsorption bed, a chlorine removal adsorption bed, a siloxane removal adsorption bed, a heat exchanger loop and a biogas precooler. Some embodiments (Continued)

of a biogas cleaning method can also include precooling the biogas waste stream, adsorbing siloxanes from the biogas waste stream and adsorbing hydrogen chloride from the biogas stream.

15 Claims, 5 Drawing Sheets

(51) Int. Cl.
| | | |
|---|---|---|
| | *C01B 17/16* | (2006.01) |
| | *C12M 1/00* | (2006.01) |
| | *B01D 53/26* | (2006.01) |
| | *B01D 53/48* | (2006.01) |
| | *B01D 53/68* | (2006.01) |
| | *B01D 53/72* | (2006.01) |
| | *B01D 53/86* | (2006.01) |

(52) U.S. Cl.
CPC ........... *C12M 47/18* (2013.01); *B01D 53/265* (2013.01); *B01D 53/48* (2013.01); *B01D 53/685* (2013.01); *B01D 53/72* (2013.01); *B01D 53/864* (2013.01); *B01D 2251/202* (2013.01); *B01D 2251/304* (2013.01); *B01D 2253/102* (2013.01); *B01D 2253/108* (2013.01); *B01D 2253/116* (2013.01); *B01D 2253/1124* (2013.01); *B01D 2255/1021* (2013.01); *B01D 2255/1023* (2013.01); *B01D 2255/1025* (2013.01); *B01D 2255/20746* (2013.01); *B01D 2255/20753* (2013.01); *B01D 2255/20769* (2013.01); *B01D 2257/104* (2013.01); *B01D 2257/20* (2013.01); *B01D 2257/30* (2013.01); *B01D 2257/55* (2013.01); *B01D 2257/708* (2013.01); *B01D 2257/80* (2013.01); *B01D 2258/05* (2013.01); *Y02C 20/20* (2013.01); *Y02P 20/129* (2015.11); *Y02P 20/59* (2015.11)

(56) References Cited

U.S. PATENT DOCUMENTS

| | | |
|---|---|---|
| 4,505,880 A | 3/1985 | Deschamps et al. |
| 6,200,544 B1 | 3/2001 | Blachman |
| 6,712,885 B1 | 3/2004 | Basseen et al. |
| 2002/0085970 A1 | 7/2002 | Sederquist et al. |
| 2007/0068386 A1 | 3/2007 | Mitariten |
| 2008/0141951 A1 | 6/2008 | Liu |
| 2008/0315158 A1 | 12/2008 | Cambra Ibanez et al. |
| 2009/0194459 A1 | 8/2009 | Vincitore et al. |

FOREIGN PATENT DOCUMENTS

| | | |
|---|---|---|
| JP | 2009530435 A | 8/2009 |
| JP | 2010180197 A | 8/2010 |

OTHER PUBLICATIONS

Hearing Notice dated Jun. 13, 2019 in connection with Indian App. No. 418/DELNP/2013.
Office Action dated Jul. 10, 2018 in connection with Korean patent application No. 10-2013-7003784.
International Search Report and Written Opinion dated Sep. 27, 2011 in connection with International Application No. PCT/CA2011/000825.
International Preliminary Report on Patentability dated Jan. 15, 2013 in connection with International Application No. PCT/CA2011/000825.
Office Action dated May 7, 2015 in connection with Japanese Application No. 2013-518915.
Office Action dated Dec. 21, 2015 in connection with Canadian Application No. 2,709,722.
Examination Report dated Jan. 10, 2018 in connection with Indian Application No. 418/DELNP/2013.

INTEGRATED BIOGAS CLEANING SYSTEM TO REMOVE WATER, SILOXANES, SULFUR, OXYGEN, CHLORIDES AND VOLATILE ORGANIC COMPOUNDS

CROSS-REFERENCE TO RELATED APPLICATIONS

This application is a continuation of U.S. application Ser. No. 13/810,197 filed on Apr. 24, 2013, entitled "Integrated Biogas Cleaning System to Remove Water, Siloxanes, Sulfur, Oxygen, Chlorides and Volatile Organic Compounds" which claims priority benefits from International Application No. PCT/CA2011/000825 filed on Jul. 15, 2011, entitled "Integrated Biogas Cleaning System to Remove Water, Siloxanes, Sulfur, Oxygen, Chlorides and Volatile Organic Compounds". This application is also related to and claims priority to the '825 application. This application is also related to and claims priority benefit from Canadian Application No. 2,709,722 filed Jul. 15, 2010, entitled "Integrated Biogas Cleaning A System to Remove Water, Siloxanes, Sulfur, Oxygen, Chlorides, and Volatile Organic Compounds".

The '197, '825 and '722 applications are hereby incorporated by reference herein in their entireties.

FIELD OF THE INVENTION

The invention relates to cleaning of waste biogas, which includes landfill gas. In particular, the present invention relates to an biogas cleaning system for removing contaminants unsuitable for use as a fuel, including water, volatile organic compounds, siloxanes, oxygen, chlorine, and sulfur to less than 50 parts per billion each by volume.

BACKGROUND

Biogas is typically a waste product from sources including anaerobic digesters, municipal waste treatment plants and landfills, or any source that organic waste is able to break down in an environment that is largely free of oxygen. Biogas typically contains approximately 50% to 75% methane, 25% to 50% carbon dioxide, 0% to 10% nitrogen, 0% to 1% hydrogen, 0% to 3% sulfur, and 0% to 2% oxygen, all by volume, as well as an assortment of trace impurities that can include siloxane, chlorine, volatile organic compounds, and ammonia. The water content of the biogas is typically saturated at temperatures slightly above ambient, for instance at temperatures up to approximately 50° C. Because biogas is typically generated from organic matter it is typically considered a renewable form of energy, such that the use of biogas as fuel liberates no new carbon to the atmosphere.

Because biogas contains methane it is convertible to a biogas fuel for power or heat generation. However, because of constraints of generator operation with contamination and emission restrictions on its use, biogas should be cleaned of its impurities first. One reason for cleaning the biogas is that biogas contains contaminants that would be harmful to the environment. For instance, the hydrogen sulfide and organic sulfurs are present in biogas at levels from a few parts per million to several thousand parts per million which, when combusted, becomes sulfur dioxide, which is a leading cause of acid rain. The other reason that biogas should be cleaned is that some impurities in biogas such as the siloxanes can be deposited within heat and power generation equipment and cause significant damage to internal components, potentially causing premature breakdowns and/or the need to maintain the equipment frequently with overhauls. Siloxanes end up in biogas because they are used in various beauty products such as cosmetics and shampoos that are washed down drains or otherwise disposed of, so they end up in municipal wastewater and landfills. Sulfur impurities in biogas can create a corrosive environment inside power generating equipment or even poison catalysts that may be present.

Gas turbines require very low levels of impurities due to the possibility of rotor un-balance from contaminant build up and due to catastrophic failure from the release of that built up debris. Fuel cells require a specification of near zero contaminants because those contaminants can build up on catalyst surfaces and degrade the output performance. Internal combustion engine specification's for contaminants are higher than both turbines and fuel cells because they are based on what can be tolerated by performing frequent and costly maintenance or equipment replacement. Therefore internal combustion engines operations could benefit from near zero contaminant levels as well since it could reduce the frequency of the maintenance cycle and therefore improve the economics of operation. Furthermore, the relatively higher impurity levels that can be handled by internal combustion engines also mean that the pollution from the internal combustion engines can be relatively higher than the other equipment.

There are other existing biogas cleanup solutions in the market, however few are able provide a cost effective approach to the removal of impurities to low enough levels that do not cause difficulties for downstream equipment such as fuel cells and generators. For instance, the desired levels of impurities that are required for clean power generation applications such as fuel cells to reduce maintenance to a minimum is typically to have less than 50 parts per billion of each of sulfur, siloxanes, halogens (chlorine, etc), and ammonia. The ongoing cost of the cleanup impacts the bottom line for energy generation equipment in terms of $/kWh operational costs because it costs money to clean the biogas up prior to use. If these cleanup costs are too high, it becomes difficult to utilize the biogas resource economically. There is a need for enhanced clean biogas fuel to enable improvement to aggregate sustainability, including downstream generation.

Some gaseous impurity removal technologies can be found in very large scales at chemical and fossil fuel processing plants. For instance, sour gas well cleanup plants typically use the Clause process to remove sulfur. Because of the complexity of these solutions large scales are required to be cost effective, for instance typically requiring that that many adjacent sour wells have a pipeline to a centralized plant. Bringing this type of process down in scale to the sizes required to process biogas at much smaller point sources such as landfills and waste treatment plants in municipalities that are spaced much further apart can be difficult as a standalone system. When complex technologies are adapted for smaller applications the system is typically simplified in order to decrease capital costs, but this can at times also inadvertently decrease the effectiveness of impurity removal. Biogas impurities can vary substantially over time, and the reduced system complexity can mean that the system does not have the capability to react appropriately, risking upsets to downstream equipment.

Many landfills are punctured with vertical and horizontal wells so that a vacuum can be created to pull out the generated biogas and flare it so that the methane in the biogas does not ingress through the surface of the landfill and contribute to global warming or climate change, since methane is many times stronger than carbon dioxide in its ability to capture heat in the atmosphere from the sun. However, when the biogas is pulled out from the landfill many other impurities are also pulled out, and these impurities inevitably end up in the atmosphere after being flared. There is a need to remove and contain impurities prior to flaring or combustion of biogas to reduce this atmospheric pollution.

From an environmental perspective a key concern with biogas cleaning solutions is where the impurities end up. For example, if a sulfur rich adsorbent regeneration gas is simply combusted in a flare then potentially high levels of sulfur end up in the atmosphere. There is an unmet need to remove these impurities before the flare or power generation equipment and replace those impurities back into the landfill in stable solid form to ensure that the polluting impurities remain out of the atmosphere. There is a need for cleaning systems that capture these impurities in a solid form.

Some of the existing solutions to remove higher levels of impurities are a class of regenerable materials, which can include a regenerative adsorbent or wash that captures the impurities while in contact with the biogas. Then at a later time the adsorbent or wash is separated from the biogas to be regenerated by a process that can include heat and/or passing a different gas over the adsorbent or wash to carry away the contaminants, among other solutions. This regeneration brings down the cost of impurity removal, however typically the contaminants end up in the atmosphere after regeneration occurs. In addition, the continuous regeneration can also affect the long-term performance of the adsorbent or wash since the regeneration process may not be able to remove the buildup of other impurities completely. Because of this the adsorbent or wash can degrade over longer periods of time, this can affect the amount of contaminant slippage that occurs. To achieve very low levels of impurity breakthrough the regenerative adsorbent or wash materials may need to be changed more frequently, adding to cost and reducing sustainable footprint.

Alternatively, some existing solutions to remove impurities from biogas and keep it in a solid form are non-regenerable adsorbent media beds. Adsorbent media captures selective impurities through adsorption while letting other molecules pass, and once their capacity is filled up they require changing. Typically the used media is placed in a landfill or otherwise disposed of. Adsorbent beds can be cost effective when handling low levels of impurities even if the capacity of the beds is small, however it can become cost prohibitive to change the beds frequently or have very large beds when there is high impurity content in the biogas, since there are both adsorbent purchase costs and disposal costs to contend with.

Another added consideration with sulfur adsorbent beds is that the capacity of the adsorbent beds typically depends upon the types of sulfur species that are to be captured. For example, the sulfur species that are most readily captured by activated carbon at near ambient temperature is hydrogen sulfide, and this allows for the greatest capacity of sulfur to build up on the activated carbon bed before breakthrough occurs, as measured by grams of sulfur per gram of virgin absorbent. However there are occasions where there are sulfur species present in biogas other than hydrogen sulfide, such as organic sulfurs, and these are typically harder to capture. For instance, activated carbon can have very high sulfur loadings when removing hydrogen sulfide, but when removing organic sulfurs the loading is greatly reduced before trace breakthroughs of sulfur occur. There is a need for a cleaning method to convert biogas sulfides to primarily hydrogen sulfide for effective removal and maximum utilization of adsorbing materials. With many sulfur adsorbents in general the capacity for H2S is much higher than other sulfur species.

In industrial processes there is a common solution to the dilemma of organic sulfur species and the lower capacity of adsorbent beds to capture them. This solution is to transform the organic species into hydrogen sulfide by providing a reducing environment, for instance with no oxygen with a small excess of hydrogen, and bringing the gas to a hydrodesulphurization catalyst bed at elevated temperatures of 250° C. to 400° C. The typical reaction on the hydrodesulfurization catalyst is to break the bonds of sulfur on any organic sulfur compounds and then replace the broken bonds of the sulfur atom with a hydrogen molecule, which is present in excess in the biogas stream. This would typically result, for instance, in a hydrocarbon molecule and hydrogen sulfide molecule. While this process doesn't remove the sulfur from the gas, the transformation of most sulfur species to hydrogen sulfide can help to maximize the cost effectiveness of downstream adsorbent beds. These same hydrodesulfurization catalysts can also hydrogenate many other species of impurities. For instance, many impurity species containing chlorine can also be hydrogenated into hydrogen chloride over the same hydrodesulfurization catalyst bed. Hydrodesulfurization catalyst is typically a sulfided form of nickel molybdenum catalyst on alumina or alternatively cobalt molybdenum catalyst on alumina, though other catalysts that would accelerate the same functional reactions could be used. There is a need for an integrated biogas cleaning process that can convert the sulfides to hydrogen sulfide efficiently and sustainably in combination with other contaminant cleaning process.

A big hurdle remains however that most biogas does not contain the hydrogen required for the hydrodesulphurization reaction to occur properly. Therefore to enable this reaction, hydrogen is required to be added to the biogas to transform the organic sulfur to hydrogen sulfide in a hydrodesulfurization reactor. There is a need to provide and integrate efficiently sources of hydrogen gas into a biogas cleaning system. A further advantage of injecting hydrogen into the biogas is that the addition of hydrogen into a fuel is known to be a way to reduce the emissions of combustion equipment such as internal combustion engines. By mixing 2% to 10% of hydrogen with fuel the flame speed can be increased and this allows leaner mixtures to be burned with complete combustion and without the possibility of misfire. Lean combustion may also be able to increase efficiency of operation in some cases. There is a need for a biogas cleaning system that integrates and efficiently provides a tailored blend of hydrogen content in a clean biogas fuel product.

There are many types of siloxane particles that can be found in landfill gas or wastewater treatment digesters. Siloxanes are known to readily breakdown into silicates when heated in the presence of oxygen, and this is what typically occurs in the combustion chambers of internal combustion engines, boilers, and turbines. It is also possible that siloxanes can be deposited on downstream catalysts in some systems such as fuel cells. The silicates formed are like fine sand particles that can be very abrasive to moving equipment, or can foul catalysts or heat exchangers. Literature suggests that siloxanes do not need to be considered an environmental hazard because they break down in the atmosphere within days. The autoignition temperature of many types of siloxanes are typically somewhere between 200° C. and 450° C.

There are various methods currently utilized to treat biogas to remove any siloxanes that may be present in the biogas. One such solution is outlined in U.S. Pat. No. 6,712,885 whereby the gas is cooled to −10° F. in order to condense out the vast majority of the siloxane molecules from the gas and most of the water. Since ice is also formed because of the water content, a special procedure is used to de-ice the heat exchangers periodically in a cyclic fashion. Another known method for removing siloxanes is to utilize a siloxane adsorbent bed. There is a need for efficiently integrating siloxane removal systems and methods into a biogas cleaning system, with efficient minimization of required power, materials and direct cost impact on converting the biogas waste to biogas fuel.

SUMMARY

An embodiment of a biogas cleaning system is provided, including:

(a) a gas control system for blending hydrogen gas into a biogas waste stream, having a hydrogen flow controller and hydrogen port, (b) A de-oxidizer catalyst bed fluidly coupled downstream of the gas control system for receiving and catalytically combusting the blended hydrogen with the remaining oxygen in the biogas such that oxygen is substantially removed from the biogas and the biogas stream is heated, (c) An hydrodesulphurization catalyst bed fluidly coupled downstream of the de-oxidizer catalyst bed that receives the heated biogas stream for the purpose of hydrogenating sulfur species to substantially hydrogen sulfide and hydrogenating chlorine species to substantially hydrogen chloride (d) A first hydrogen sulfide removal adsorption bed fluidly coupled downstream of the hydrodesulphurization catalyst bed for the purpose of substantially removing sulfur from the biogas, (e) A thermal sensor controller for measuring biogas stream temperature and in communication with the gas control system, such that when operable and receiving a biogas stream, hydrogen is mixed with the biogas, then the oxygen is substantially removed, the biogas stream is heated sufficiently by the exothermic combustion such that the sulfur species are hydrogenated by the hydrodesulphurization catalyst bed being converted primarily to hydrogen sulfide, then the converted hydrogen sulfide is substantially removed the adsorbent bed, and further the rate of hydrogen blending is controlled in response to the thermal sensor controller.

An additional detailed embodiment of a biogas cleaning system is further provided, including, (a) a biogas pre-cooler for reducing volatile organic compounds and water in the biogas waste stream, (b) a siloxane removal adsorption bed fluidly coupled downstream of the biogas pre-cooler for substantially removing siloxanes from the biogas (c) a gas control system for blending hydrogen gas into a biogas waste stream, having a hydrogen flow controller and hydrogen port downstream of the siloxane removal adsorption bed, (d) A de-oxidizer catalyst bed fluidly coupled downstream of the gas control system for receiving and catalytically combusting the blended hydrogen with the remaining oxygen in the biogas such that oxygen is substantially removed from the biogas and the biogas stream is heated, (e) An hydrodesulphurization catalyst bed fluidly coupled downstream of the de-oxidizer catalyst bed that receives the heated biogas stream, (f) a chlorine removal adsorbent bed downstream of the hydrodesulfurization catalyst and upstream of the first sulfur removal adsorbent bed, (g) A first hydrogen sulfide removal adsorption bed fluidly coupled downstream of the hydrodesulphurization catalyst bed, (h) A sulfur polisher adsorption bed fluidly coupled downstream of the first hydrogen sulfide removal adsorption bed in order to remove trace sulfur levels from the biogas (i) A thermal sensor controller for measuring biogas stream temperature and in communication with the gas control system, (j) A heat exchanger fluidly coupled downstream of hydrogen port and upstream of deoxidizer catalyst bed and to heated biogas stream exiting the hydrogen sulfide removal adsorption bed, wherein the cool heat exchange loop is formed of incoming biogas stream and outgoing cooled clean biogas, and the hot heat exchange loop is formed of outgoing clean heated biogas stream and the biogas stream upstream of de-oxidizer catalyst bed further including a biogas flow controller fluidly coupled to sulfur polisher adsorption bed, heat exchanger and outgoing cooled clean biogas stream and operable to distribute the hot clean biogas stream between the hot or cool exchange loops and heat exchanger such that when operable and receiving a biogas stream, siloxanes, VOC's and water is substantially removed, then hydrogen is mixed with the biogas, flow and temperature of the hot biogas returning to the economizer heat exchanger is adjusted to maintain the biogas temperature downstream of the de-oxidizer catalyst bed in a range 250° C. to no higher than 400° C. such that remaining oxygen is removed and the biogas stream is heated such that the sulfur species are hydrogenated by the hydrodesulphurization catalyst bed being converted primarily to hydrogen sulfide, then halides are removed prior to absorbing sulfides to produce a clean biogas fuel.

An embodiment of a biogas cleaning method is further provided, including the steps of, (a) Blending hydrogen with a biogas waste stream using a gas control system, (b) Combusting the blended hydrogen and biogas stream to remove oxygen and heat the biogas to a range 250° C. to no higher than 400° C., (c) Then hydrogenating the resulting heated biogas stream, converting sulfides to substantially hydrogen sulfide, (d) Then absorbing hydrogen sulfide, (e) Controlling the hydrogen concentration in response to temperature following step (b), such that a substantially clean biogas fuel is provided.

An embodiment of a biogas cleaning method is further provided, including the steps of, (a) pre-cooling a biogas waste stream reducing volatile organic compounds and water, (b) adsorbing siloxanes and substantially removing siloxanes from the biogas waste stream (c) then adding hydrogen gas in the biogas stream, (d) catalytically combusting the blended hydrogen with the remaining oxygen in the biogas such that oxygen is substantially removed from the biogas and the biogas stream is heated, (e) then hydrogenating sulfur species to substantially hydrogen sulfide and simultaneously hydrogenating chlorine species to hydrogen chloride (f) then adsorbing hydrogen chloride, (g) then adsorbing hydrogen sulfides using a sulfur adsorbent, (h) then further adsorbing remaining hydrogen sulfides using a sulfur polisher (i) adjusting flow and temperature of the hot biogas returning to the economizer heat exchanger to maintain the biogas temperature downstream of the de-oxidizer catalyst bed in a range 250° C. to no higher than 400° C., such that a substantially clean biogas fuel is provided.

The benefits of the biogas cleaning system and method embodiments include converting contaminated raw biogas waste to clean biogas fuel such that very low levels of impurities such as sulfur, siloxanes, chlorine, and oxygen remain in the biogas after cleaning so that the resulting biogas is usable as a fuel for power generators and contaminant sensitive fuel cell systems.

DETAILED DESCRIPTION OF ILLUSTRATIVE EMBODIMENTS

Biogas cleaning systems and methods are provided that meet the needs described in the background. There are specialized challenges and hurdles of designing and integrating various conflicting stages of contaminant removal and to reach the extreme low concentrations of contaminants. Providing an efficient and streamlined integrated biogas cleaning system that is optimized to remove the various biogas contaminants in a novel sequence and combination of techniques, requires novel and new designs to integrate and compensate for each stage processing conditions, materials requirements and effective input temperatures and degree of remaining contaminant concentrations. The embodiments described herein have solved these various unmet needs in an efficient, effective and integrated manner, and specific solutions to each need and novelty is described where most relevant.

Referring more specifically to the drawings, for illustrative purposes the biogas system is embodied in the systems generally shown in FIG. 1-5, schematically. Fluid lines are shown with direction of fluid (e.g. biogas) flow. It is assumed that fluid line connections between elements incorporate any standard fittings, couplers, and sensors common and known to one skilled in the art of gas cleaning systems and necessary to build the biogas cleaning system, may, if not shown explicitly, be considered to be incorporated in the detailed embodiment. Similarly for reactor beds as commonly used in gas cleaning may have independent heaters and thermal control systems—these are not shown explicitly but assumed included in the definition of "bed". For convenience of explanation, reference is made to the gas stream by number of the associated fluid line, and it is assumed there is an associated fluid line for each described gas stream.

Figure 1:
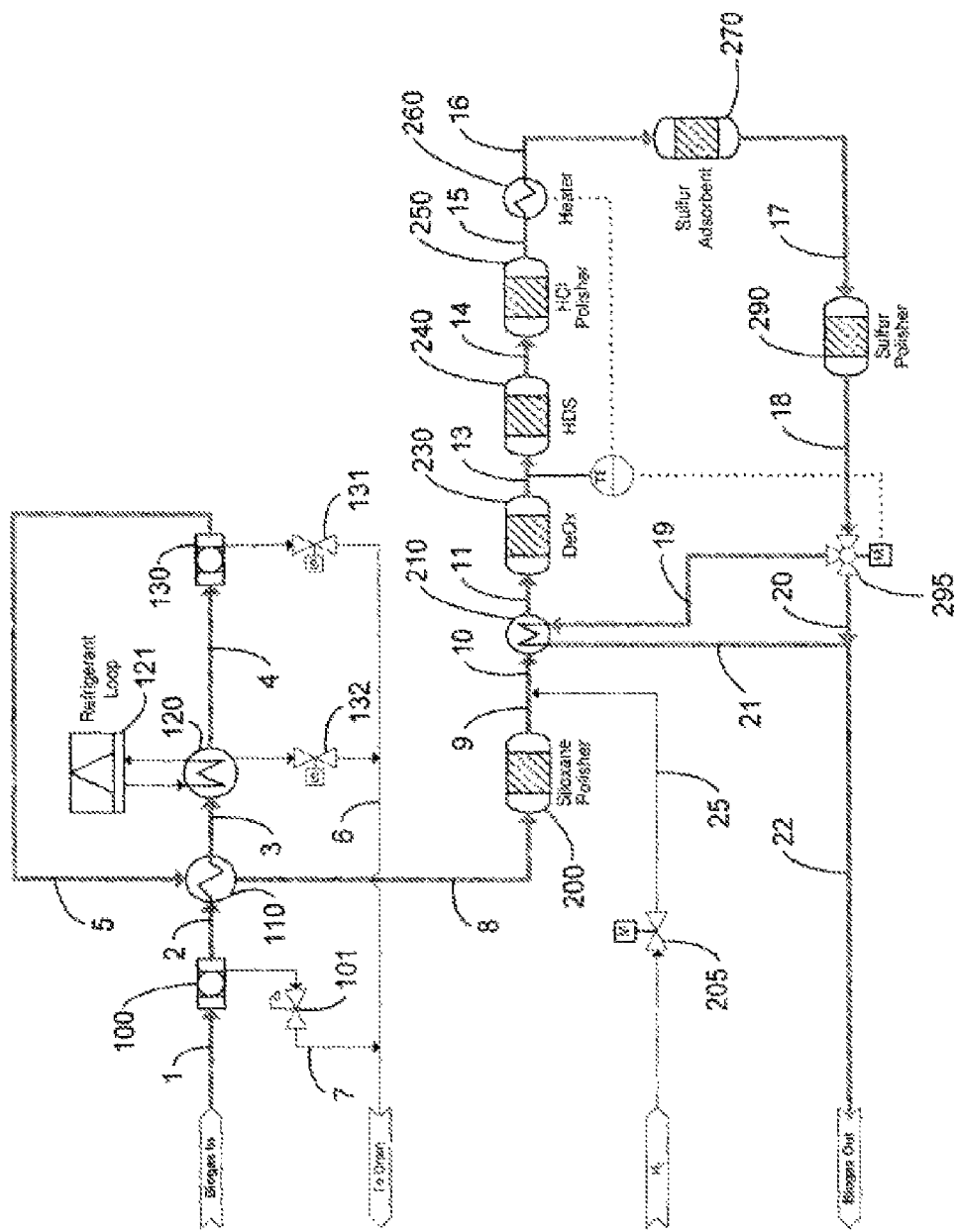
FIG. 1 is a schematic flow diagram illustrating the preferred embodiment of a combination of elements of a biogas cleaning system for removing siloxane, oxygen, chlorine, and sulfur species to parts per billion levels, and a pre-cooling stage to remove the majority of water and volatile organic compounds.

A preferred embodiment of a biogas cleaning system 111 is shown in FIG. 1. On the left, various inputs and outputs are shown (as discussed only the fluid lines are shown, not common fittings and ports that would be incorporated in a product by an engineer skilled in the art). A biogas waste stream 1 enters an optional water removal system 112 indicated by the dashed box, which outputs a waste liquid 6. Following this initial water removal system 112, biogas stream 8 enters additional integrated contaminant removal stages which are essential to reduction of key contaminants to very low levels. The biogas waste stream can originate from a digester, landfill, industrial process or sewage treatment. Biogas typically contains approximately 50% to 75% methane, 25% to 50% carbon dioxide, 0% to 10% nitrogen, 0% to 1% hydrogen, 0% to 3% sulfur, and 0% to 2% oxygen, all by volume, as well as an assortment of trace impurities that can include siloxane, chlorine compounds, sulfur compounds, volatile organic compounds, and ammonia. The water content of the biogas is typically saturated at temperatures slightly above ambient, for instance up to 50° C. The gas cleaning system 111 is operable over this wide range of biogas contaminant concentrations, however with various compensations required depending particularly on hydrogen and oxygen content.

The water removal system 112 cools and condenses out water, volatile organic compounds, and siloxanes from the biogas waste stream 1. This is done as a precursor stage as downstream systems are inoperable or ineffective with water content and too high a level of contaminants. For example such removal prior to the hydrodesulfurization catalyst bed 240 is required to protect this bed and other catalyst and adsorbent beds in the system from premature poisoning from siloxanes. Therefore the life of these catalysts and adsorbents is maximized and the change out of beds is reduced to a minimum, improving the economics of biogas cleaning overall. Of course, by protecting the catalysts and components within the biogas cleaning system, downstream power generation equipment is protected from the same potential damage. A further advantage with the cooling and condensing subsystem is that the water is removed from the biogas. This water removal augments downstream equipment such as the sulfur adsorbent beds since the slip of sulfur through those beds is reduced with decreasing water levels. For instance, zinc oxide adsorbent equilibrium slip levels of hydrogen sulfide move from approximately 1 part per million at high water levels to below 100 part per billion with low water levels while at operating temperatures of around 400° C. In addition, the relative humidity of the biogas going to internal combustion engines should be below a certain threshold to avoid condensation on internal components. Typically while the water is condensing out of the biogas there are other impurities that are partially absorbed in the condensed water, especially hydrogen sulfide and sulfur dioxide, which reduces the burden on the downstream sulfur adsorbents stage.

Referring to FIG. 1, with the preferred embodiment there is a biogas source that is able to introduce biogas waste stream 1 into the biogas cleaning system 111. Typically biogas stream 1 is saturated or nearly saturated with water so one of the first steps in the biogas cleaning system is to remove liquid water with separator 100 and create liquid stream 7 when the separator is periodically drained with float valve 101. The single phase biogas stream 2 then enters into the optional cold economizer heat exchanger 110 having a cold loop as represented by gas streams 3, 4, 5. The biogas is initially cooled by the cold biogas stream 5 that is leaving the cold loop as defined by the cold side of cold recuperative heat exchanger 100, in order to reduce the power consumption required by the refrigeration system 121. Biogas stream 3 then leaves the cold recuperative heat exchanger and enters into the refrigeration heat exchanger 120 where the biogas is further cooled to between 40° F. or −10° F. or less. Biogas stream 4 leaving heat exchanger 120 is at the coldest point in the system and therefore has the least amount of siloxanes, water, and volatile organic compounds in the gaseous phase, which have condensed. The liquids that have been condensed in biogas stream 4 are then partially separated from the gas in coalescing filter or separator 130 and the liquids are removed periodically from the separator by opening solenoid valve or drain trap 131. In addition, when the solids that are formed within refrigerant heat exchanger 120 are defrosted then the liquids that fall out can be removed from the system with solenoid 132 and mixed with the liquids from solenoid 131 to become liquid stream 6. Biogas stream 5 coming from coalescing filter or separator 130 then flows through heat exchanger 110 to cool the incoming gas and then leaves the condensing subsystem as biogas stream 8, now having concentration of water, siloxanes, and volatile organic compounds greatly reduced, suitable for the next stage of gas cleaning.

Available cooling and condensation methods using water removal system 112 are discussed in more detail. While it is generally preferable that the biogas be cooled to −10° F. in order to condense out the majority of the siloxanes and some of the volatile organic compounds, this low temperature does not necessarily need to be reached in some cases, to be effective. Since some biogas sources such as agricultural digesters do not have any siloxanes or volatile organic compounds impurities, in these cases it is be sufficient to reduce the temperature of the biogas to around 40° F. in order to remove most of the water only. This is also the case if the siloxane levels in the biogas waste stream 1 are very low, for instance less than approximately 1 part per million, where it would be possible to simply capture most of the siloxanes economically with the downstream siloxane removal bed. The water removal is potentially also a requirement in order to meet the specifications of power generation equipment using the biogas fuel produced. Because these advantages are not necessarily rigid requirements in every application, it is possible that no cooling of the inlet gas is required in some applications and cooling subsystem components 110, 120 and 121 are not required for operation.

Having left the water removal stage, the biogas stream 8 enters into siloxane polisher adsorbent bed 200 containing an adsorbent that is able to capture remaining siloxanes in the biogas. The adsorbent bed is preferably designed so that even if sulfur is also captured by the bed and the bed becomes fully saturated with sulfur, that the capacity for siloxanes is only marginally affected. Specially designed siloxane capture beds such as FCDS-GS25A from Sud Chemie are to our understanding able to do this at some capacity. Since within biogas stream 8 there are only trace amounts of siloxane left in the biogas while the bulk of the sulfur remains, the sulfur capacity of bed 200 quickly is filled during operation while there remains much more life left in the bed for its primary purpose of removing trace levels of siloxane. If there are no siloxanes present in a particular biogas waste application, then the siloxane adsorbent bed 200 is optional.

As apparent in later stages, hydrogen is required to be blended with the biogas stream prior to a downstream combustion and hydrodesulfurization process. The preferable insertion of hydrogen stream 25 is following siloxane polisher 200 between biogas stream 9 and the blended biogas and hydrogen stream 10. Biogas stream 9 leaves the siloxane polisher bed 200 and mixes with the hydrogen stream 25, which itself is controlled by control valve 205 such that there is a minimum of 2% hydrogen in the biogas stream 10. The flow rate of hydrogen stream 25 is controlled by flow controller (such as a motorized valve) 205. Hydrogen flow controller 205 can optionally be in communication (not shown) with thermal sensor TE to control the hydrogen rate in response to a desired temperature in the system. In specific applications where a fuel cell powerplant (not shown) and resulting product streams are available, there is typically a slipstream of hydrogen that can be utilized for this process. Hydrogen can also be created from the biogas itself, for instance by reforming (not shown) the methane in a slipstream of the biogas, particularly a recycle of the clean biogas 22 leaving the system. Addition of hydrogen also provides a benefit of optional tailored blend of hydrogen content in a clean biogas fuel product, as excess hydrogen can propagate through to the biogas fuel product.

The biogas proceeds through additional stages of contaminant removal sequentially through cleaning elements as biogas streams 10,11,13,14,15,16,17,18,19, forming a hot side of an economizer heat exchanger 10. The functionality of the heat exchanger is described further on in this description for each individual cleaning element in the hot side loop. Bio gas stream 10 enters the hot recuperative heat exchanger 10 and is preheated by downstream clean biogas stream 19. Typically heat exchanger 210 is a large heat exchanger that is able to preheat the gas as much as possible so that the biogas stream 11 is efficiently heated and clean outlet biogas stream 21 is efficiently cooled. However, in the case when there is a larger amount of oxygen in the biogas stream 11 such that the exothermic temperature rise in the downstream de-oxidizer catalyst bed 230 (labeled DeOx) is large and such that the outlet temperature of biogas stream 13 is hotter than what is allowable by the downstream hydrodesulfurization catalyst bed 240 (labeled HDS), then the flow rate of clean biogas stream 19 into the heat exchanger 210 is reduced by bypass control valve 295 so that more of the clean hot biogas from stream 18 is diverted directly through biogas stream 20, to compensate. This is done in order to avoid there being too much heat input into the hot loop defined by the hot side of the economizer heat exchanger 210 and therefore to avoid any thermal runaway of temperatures in that hot loop. In this way, bypass control valve 295 effectively allows the biogas cleaning system to operate with high oxygen concentrations in the biogas before shutdown would need to occur. This provides a benefit of being tolerable to a wide range of potential and varying oxygen concentrations in the raw waste biogas input.

From the heat exchanger 210, biogas stream 11 enters into a de-oxidizer catalyst bed 230. The system 111 is able to control the temperatures that the hot components in the hot side operate at under a relatively large band of inlet oxygen concentrations. Because the oxygen is combusted with hydrogen in the de-oxidizer catalyst bed there can be a relatively large exothermic temperature rise with the reaction. An example of a suitable material is FCR-HC25B from Sud Chemie for a de-oxidation catalyst bed. If there is too much heat addition the temperature in the hot loop that is defined by the hot side of the economizer heat exchanger, thermal runaway occurs. In order to dump heat some of the hot clean biogas going to the recuperative heat exchanger is bypassed as required. Alternatively, when there is not enough of an exothermic temperature rise in the de-oxidizer catalyst bed then the heater is activated to inject energy into the hot loop increasing the temperature therein. In that bed 230 the hydrogen that is present in the biogas is able to combust any and most of the remaining oxygen in the biogas stream, causing an exothermic temperature to rise in proportion to the oxygen concentration, producing water byproduct. The outlet temperature of the de-oxidizer catalytic bed in biogas stream 13 would be monitored (TE thermal sensor—not numbered) to make sure that it remains within the hydrodesulfurization operating temperature window, and appropriate control of the bypass valve would occur as outlined in the above paragraph. The temperature (TE thermal sensor) in biogas stream 13 can additionally be used as control feedback for a heater 260 in the case that there is insufficient exothermic temperature rise in the de-oxidizer bed. In operation, maintaining the biogas stream temperature within suitable range for the de-oxidizer catalyst bed 230, is provided by programming the thermal element in biogas stream 13 to control either one of the heater 260 or the bypass control valve 295 and not both at the same time, such that if there is too much oxygen the heater is switched off and the bypass valve is in operation, or alternatively if there is not enough oxygen then the bypass valve ensures that the biogas stream 20 has no flow while the heater 260 is operational.

Since a hydrodesulfurization catalyst bed is essential to the system 111 and since oxygen is often present in biogas, the de-oxidizer catalyst bed 230 is utilized to allow the hydrogen mixed into the biogas to combust with any oxygen that is still present in the biogas at a temperature that is lower than the auto-ignition temperature of hydrogen in air. This is done prior to the hydrodesulfurization catalyst bed 240 in order to protect that bed from damage due to oxygen in the biogas. If a platinum catalyst (similar to an emission control catalyst from a vehicle) that is sufficiently robust to the presence of moderate levels of sulfur is used, then the ignition temperature of hydrogen and oxygen can be around 200° C. or even less. Extra hydrogen is required to be added to the biogas if the oxygen content is higher than a negligible amount. Specifically enough hydrogen needs to be added to ensure that the minimum amount of hydrogen is still available for the hydrodesulfurization reaction, of about 2% by volume. For every 1% of oxygen that is present in the biogas an extra 2% of hydrogen is needed to be added over and above the 2% required for the hydrodesulfurization reaction. Following the DeOX stage, the biogas stream 13 has reduced water, oxygen and contaminant content, and is heated at an appropriate temperature preferably between 300° C. and 400° C. suitable for further sulfide cleaning in hydrodesulfurization catalyst bed 240 (HDS). It is noted this temperature range is adjustable as new products or materials are available. Within this catalyst bed 230 there is usually no appreciable temperature rise when the impurities that are hydrogenated are generally only trace part per million amounts. Within this bed most sulfur species are hydrogenated to hydrogen sulfide and most chlorine species are hydrogenated to hydrogen chloride so that the impurities are easier to remove in downstream adsorbent beds. The de-oxidizer catalyst bed can be placed within the same vessel as the hydrodesulfurization vessel as long as the beds remain separated by a perforated metallic plate or by having the upper catalyst being of a larger size than the lower catalyst.

The benefits and novelty of this stage with the hydrodesulfurization catalyst bed 240 is that any sulfur and chlorine species present in the biogas can be hydrogenated to hydrogen sulfide and hydrogen chloride so that they can be easily removed and so that very low levels of these impurities are seen at the outlet of the biogas cleaning system regardless of what kinds of sulfur or chlorine species may be present in the inlet biogas to the system. A suitable material is HDMax 200 from Sud Chemie for a hydrodesulfurization catalyst bed. Approximately 2% hydrogen needs to be present in the biogas for this conversion process to occur and the temperature in the hydrodesulfurization catalyst bed needs to be kept above 250° C. to ensure sufficient activity and below 400° C. to avoid the reverse shift reaction due to the carbon dioxide that is also present in the biogas. Without this transformation step some species of sulfur and chlorine in biogas can be difficult to capture with adsorbent beds, such that they either slip through adsorbent beds or such that the adsorbent bed capacities are greatly reduced. Therefore, by transforming these species it is possible to get better economics by having to change the adsorbent beds less frequently while also ensuring that downstream equipment such as fuel cell systems are not slowly poisoned. This stage provides the benefit of a cleaning system that converts biogas sulfides to primarily hydrogen sulfide for effective removal and maximum utilization of adsorbing materials.

Next, the biogas stream 14 exits the hydrodesulfurization catalyst bed 240 and enters into the hydrogen chloride removal adsorption bed 250 (commonly referred to as HCL Polisher). In this bed 250, the hydrogen chloride that is present in the biogas is adsorbed into the bed. An example of suitable material is ActiSorb CL2 from Sud Chemie for a hydrogen chloride removal bed. The placement of this bed is preferentially upstream of the sulfur removal bed 270 in order to protect bed 270 from poisoning by the chlorine in the biogas. If there is no chlorine in the biogas in a particular application or installation, then the chlorine removal adsorbent bed is optional and can be omitted. The location of the chlorine removal adsorbent bed can also be placed upstream of the hydrodesulfurization reactor bed though it may not have as high a capacity for other chloride species other than hydrogen chloride.

Several of the contaminant removal stages vary with temperature and so maintaining the biogas stream temperature within the ranges for each stage as previously described is a necessary condition, in some cases requiring an optional supplementary heater 260. The biogas exits the hydrogen chloride removal adsorption bed 250 as biogas stream 15 and then enters into heater 260. This heater 260 can be an electrical heater or it can be a heat exchanger utilizing a controllable hot fluid such as burner gas to heat the biogas. Heater 260 is shown in a preferential location that ensures that the sulfur adsorbent bed 270 is at the maximum possible temperature while ensuring that the hydrodesulfurization temperature is at or below its maximum temperature as measured by the thermal element at biogas stream 13. In various alternate embodiments however, the heater (or heaters) can also be placed at any location within the hot loop as defined by the hot side of the recuperative heat exchanger 210, including being incorporated within a catalyst or adsorbent bed to also ensure that a bed remains hot during shutdown or can heat up independently of there being any biogas flow in the system. In these case, additional thermal sensors (not shown) such as standard thermocouples are optionally associated with each heater controller (not shown) which is set as required to maintain a specific stage temperature as is common in the art.

At this stage of biogas stream 16, the sulfides have previously been substantially converted to hydrogen sulfide and now the hydrogen sulfide is removed in a sulfur adsorbent bed 270. The removal of water is advantageous because it helps the equilibrium on the sulfur adsorbent and reduces the amount of hydrogen sulfide that slips through that bed and therefore reduces the burden on the sulfur polisher. A suitable active material incorporated in the bed is ActiSorb S2 from Sud Chemie forming a high temperature zinc oxide bed. The preferential media for this bed is zinc oxide because of the high sulfur capacities that are possible. There are various ways to increase the capacity of sulfur adsorbent beds. One way is to increase the operating temperature. Zinc oxide can have a capacity in excess of 30 grams of sulfur per 100 grams of virgin zinc oxide if it is able to operate at 400° C. to 600° C. This bed can optionally be made up of two beds in series, for instance in a standard lead/lag arrangement (not shown) with 4 or 6 valves (not shown) that allow one bed to be isolated and the adsorbent media changed while the other bed is still operational. The lead/lag arrangement allows the sequence of beds to be switched which enables the front bed to be fully saturated with sulfur while the second bed still has not undergone breakthrough, improving utilization and increasing system uptime. The outlet concentration of sulfur varies depending upon various factors such as how much water vapor is in the biogas, the adsorbent operational temperature, and the type of adsorbent utilized. The biogas cleaning system 111 produces sulfur levels below 50 ppb, however it is appreciated due to the wide range of biogas waste inputs that for some applications, concentration can be higher than the target of 50 parts per billion of sulfur.

In the gas processing industry, a sulfur adsorbent that is commonly used after a hydrodesulphurization reactor is pelletized zinc oxide because the temperature of operation is similar to the hydrodesulfurization reaction and the zinc oxide absorbent can have a high sulfur loading capacity. Alternatively, iron sponge absorbents can also be used for the same reason. Both zinc oxide and iron sponge absorbents have an equilibrium sulfur level that dictates how much sulfur slips through the bed. This equilibrium level is dependent upon various factors, including temperature and water content. Because the equilibrium levels for both adsorbents are typically not low enough for fuel cells if the capacity in these beds is to be maximized (e.g. while operating as hot as possible), it is known that a sulfur polisher bed that can include copper or nickel can be added after the primary sulfur adsorbent to remove any remaining sulfur in the biogas so that the biogas has less than 50 parts per billion of sulfur.

Following treatment in the sulfur adsorbent bed, trace amounts of sulfur are still potentially present in biogas stream 17. Depending on use of the biogas fuel product, an optional additional fine removal of sulfur may be required, specifically for biogas use in fuel cell systems requiring very low concentrations of sulfur. When the biogas fuel is intended for combustion generators, this fine removal is not required or is optional. This optional sulfur removal is shown as sulfur polisher bed 290 receiving biogas stream 17 from the sulfur adsorbent bed. The sulfur polisher adsorbent bed 290 removes any trace sulfur that is still present in the biogas by utilizing an adsorbent such as reduced copper, which has a high affinity for sulfur, allowing very low parts per billion levels of sulfur to pass through. A suitable active material for sulfur polisher bed 290 is ActiSorb S6 from Sud Chemie for a copper based sulfur polisher bed. This bed 290 has a reduced capacity and a higher unit price compared to the upstream sulfur absorbent bed 270 but because the capture is so negligible this bed typically lasts a very long time before needing to be changed.

At this stage all the contaminant removal steps are completed. The contaminants removed from the biogas are substantially captured in solid state form—this is critical to overall pollution reduction and sustainability compared to known biogas treatments that typically burn or flare the biogas with the contaminants that are reintroduced as toxic pollution back to the atmosphere. The captured material can be stored relatively inertly or separated from the active material and stored back in stable form in for example the original landfill—this is preferable to combusting it into the atmosphere. The biogas cleaning system provides the benefit of removing and containing impurities in a solid form, prior to downstream flaring or combustion of biogas to greatly reduce atmospheric pollution by the contaminants.

The "cleaned" and treated biogas stream 18 is hot from the various stages and needs to be typically cooled for use as a biogas fuel product. For enhanced overall efficiency, reliability and sustainable operation, the biogas heat is now recovered for efficiency in the novel thermal arrangement of the hot loop heat exchange. Biogas stream 18 enters into bypass valve 295 which has output fluid line couplings to economizer heat exchanger 210 through fluid line 19 and to biogas output line 22 through bypass fluid line 20. In typical operation of biogas cleaning system 111, bypass valve 295 is set such that the biogas flow goes into biogas stream 19 and flow through recuperative heat exchanger 210 preheating the incoming biogas stream 10 and reducing temperature of the output biogas fuel product streams 21 and 22. The exception is when the incoming biogas stream 10 contains a large amount of oxygen—this may occur with a specific bio-waste material source generating higher oxygen content. In this case, the higher oxygen content would increase combustion in DeOX stage 230 increasing the temperature above the efficient range. The bypass valve in this case is responsive to thermal sensor TE (not numbered) and has a setpoint such that some of stream 18 is passed through fluid lines 20 to fluid line 22 as a bypass and heat is removed from the hot loop defined by the hot side of economizer heat exchanger 210. Bio gas stream 21 is on the cold side of recuperative heat exchanger 210 and mixes with the heated bypass biogas stream 20 to make up biogas stream 22, which exits the system as warm and clean biogas. If the temperature of biogas stream 22 needs to be cold in this example of some flow being bypassed through biogas stream 20, then optionally an air cooled radiator (not shown) on biogas stream 20 cools the biogas before mixing with biogas stream 21. This novel arrangement provides flexibility to manage a wide range of incoming oxygen concentrations, efficiently reuses a portion of the necessary heating to reduce heater load and power inputs and has high reliability due to fewer control components and setpoints.

A novel advantage of the biogas cleaning system is the ability to operate under a large band of operation and inputs. Since the biogas formation processes can be prone to upsets, the biogas concentration can vary substantially over the life of the system. The biogas cleaning system embodiments are able to handle up to 1.5% to 2% oxygen in the biogas as well as impurities levels in the low hundreds of part per million for each species of sulfur, siloxanes, and chlorine, although the higher impurity levels impact the economics of operation since the adsorbent beds need to be changed more frequently.

Another novel benefit of the biogas cleaning system is the order in which impurities are removed in the preferred embodiment, to ensure that each subsequent operation is sufficiently protected from other impurities that may damage it—for reliable and economical operation. First the majority of siloxanes and some volatile organic compounds are removed because these can contaminate downstream catalyst and adsorbent beds, for instance when these compounds degrade in the presence of heat and form solids that can coat catalyst and adsorbent surfaces. The condensing step also reduces the contaminant removal duty on the siloxane adsorbent bed 200 since there is up to 95% less siloxanes that need to be captured by this bed, which essentially means that the replacement of this bed is more economically feasible, with operating costs approximately 95% less than without the condensation step. The next step in the sequence is to remove the oxygen from the biogas stream by DeOx bed 230, ensuring that the hydrodesulfurization catalyst is not oxidized and stripped of the adsorbed sulfur upon its catalytic surfaces that assist with the hydrogenation reaction. Again, with this sequence of steps the downstream equipment is protected, for if the hydrodesulfurization catalyst bed 240 stops working properly then there is premature breakthrough of sulfur and chlorine from the adsorbent beds 270 since the sulfur and chlorine species are not solely be in the form of hydrogen sulfide and hydrogen chloride. The next step after the hydrodesulfurization catalyst reaction is the chlorine removal with a hydrogen chloride adsorption bed 250 since the downstream sulfur adsorbent bed 270 can potentially become poisoned by any chlorine in the biogas. Finally, there are the two stages of sulfur removal, with first the bulk removal at sulfur adsorbent bed 270 with a high capacity and inexpensive bulk sulfur adsorbent such as zinc oxide, followed by a sulfur polisher adsorbent bed 290 such as reduced copper on alumina. This preferred order optimizes utilization and minimizes replacement frequency and cost of the active materials, and these efficiency benefits enable greater widespread adoption of the biogas cleaning system and a net benefit to society of recycling biogas as fuel and removing toxic contaminants as solid waste that is effectively stored with reduced atmospheric pollution.

A biogas cleaning method as described for biogas cleaning system 111, includes the following preferred steps:
a) pre-cooling a biogas waste stream reducing siloxanes, volatile organic compounds and water,
b) adsorbing siloxanes substantially removing siloxanes from the biogas waste stream,
c) then adding hydrogen gas in the biogas stream,
d) catalytically combusting the blended hydrogen with the remaining oxygen in the biogas such that oxygen is substantially removed from the biogas and the biogas stream is heated,
e) then hydrogenating sulfur species to substantially hydrogen sulfide and simultaneously hydrogenating chlorine species to hydrogen chloride,
f) then adsorbing hydrogen chloride,
h) then adsorbing hydrogen sulfides using a sulfur adsorbent,
i) then further adsorbing remaining hydrogen sulfides using a sulfur polisher,
j) adjusting flow and temperature of the hot biogas returning to the economizer heat exchanger to maintain the biogas temperature downstream of the de-oxidizer catalyst bed in a range 250° C. to no higher than 400° C., such that a substantially clean biogas fuel is provided.

Figure 2:
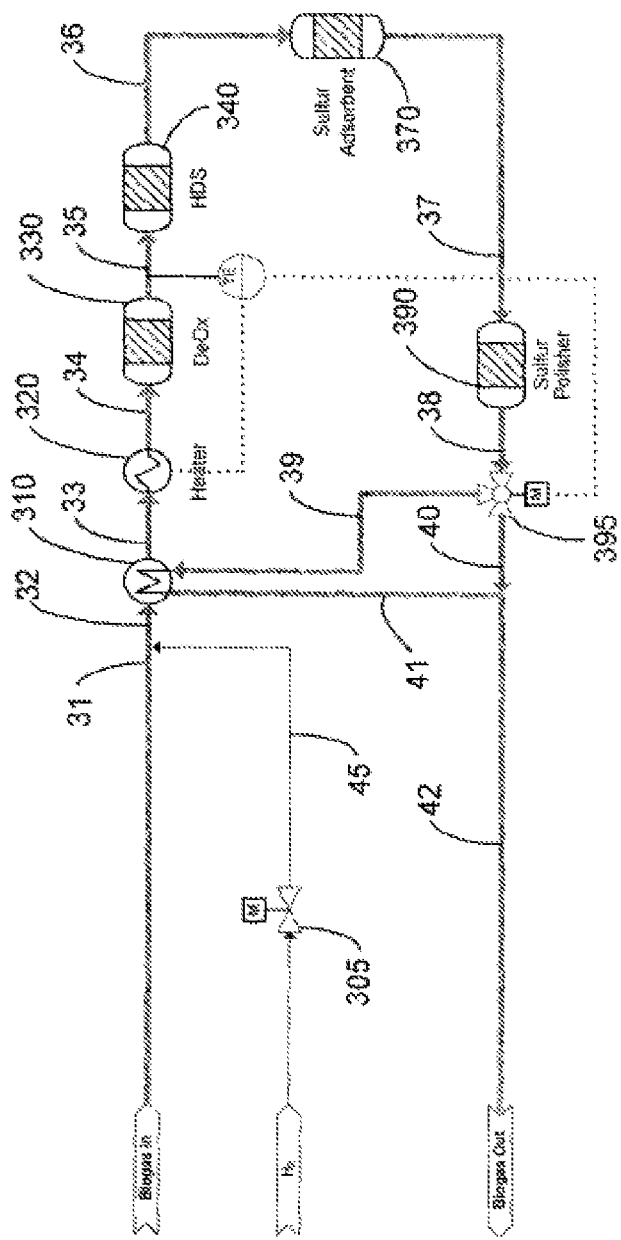
FIG. 2 is a schematic flow diagram illustrating an embodiment of a biogas cleaning system with fewest necessary elements for removing oxygen and sulfur species to parts per billion levels with the sulfur adsorbent beds operating at roughly the same temperature as the hydrodesulfurization catalyst bed.

The biogas cleaning system 111 of FIG. 1 provides a complete system for biogas treatment through conversion to biogas fuel. In an alternate embodiment, a portion of the treatment cleaning is described that can be integrated as a standalone subsystem. This is useful for example to enhance an existing biogas treatment system or in specific cases where the biogas waste is more homogeneous and has reduced contaminants requiring the other stages. Referring to FIG. 2, with another embodiment of a biogas cleaning system 222, the cooling subsystem, the siloxane removal adsorbent bed, and the hydrogen chloride removal adsorbent bed are removed to provide biogas cleaning with the fewest required elements. The biogas cleaning components and functionality are similar to those having the same name and as described in FIG. 1, but the processing components are provided in a different arrangement. The biogas enters the system 222 in biogas stream 31 and then is mixed with hydrogen stream 45, which is controlled by control valve 305 to provide a minimum of 2% hydrogen in biogas stream 32. Biogas stream 32 then enters into recuperative heat exchanger 310 to be preheated by the clean hot biogas stream 39 and exits as heated biogas stream 33. Biogas stream 33 then enters into heater 320 where heat is added to ensure that the temperature at biogas stream 35 is sufficiently high enough for the operation of hydrodesulfurization catalyst bed 340. Biogas stream 34 leaves heater 320 and enters into de-oxidizer catalyst bed 330 (DeOx) where an exothermic reaction takes place and the oxygen in the biogas is consumed by combusting some of the hydrogen. Biogas stream 35 leaves the de-oxidizer and then enters into hydrodesulfurization catalyst bed 340 (HDS) in order to hydrogenate the sulfur species present in the biogas to hydrogen sulfide. Biogas stream 36 leaves the hydrodesulfurization catalyst bed and enters into the primary sulfur adsorbent bed 370 where the majority of the hydrogen sulfide is adsorbed and therefore removed from the biogas. Biogas stream 37 leaves the primary sulfur adsorbent bed 370 and enters into the sulfur polisher adsorbent bed 390 to remove any remaining sulfur to parts per billion levels. The biogas cleaning system 222 is well suited for providing biogas fuel of quality for a fuel cell generator.

Then, biogas stream 38 leaves the sulfur polisher adsorbent bed 390 and enters control valve 395 which preferentially diverts the biogas to biogas stream 39 so that it can transfer heat through recuperative heat exchanger 310. If the amount of oxygen in the biogas inlet to the system is too high and the resultant heat input at the de-oxidizer catalyst bed 330 would cause thermal runaway in the hot loop defined by the hot side of economizer heat exchanger 310, then some of the biogas from biogas stream 38 can be bypassed or diverted around the recuperative heat exchanger 310 through biogas stream 40 so that the temperature at biogas stream 33 is reduced and the temperature at biogas stream 35 falls within the required temperature range. Leaving economizer heat exchanger 310 is biogas stream 41 which mixes with biogas stream 40 to become biogas fuel product stream 42.

A biogas cleaning method using the biogas cleaning system 222 has the following steps:
a) blending hydrogen with a biogas waste stream using a gas control system,
b) combusting the blended hydrogen and biogas stream to remove oxygen and heat the biogas to a range 250° C. to no higher than 400° C.,
c) then hydrogenating the resulting heated biogas stream, converting sulfides to substantially hydrogen sulfide,
d) then absorbing hydrogen sulfide,
e) controlling the hydrogen concentration in response to temperature following step b), such that a substantially clean biogas fuel is provided.

Similar to the rationale for system 222 in FIG. 2, another embodiment is shown in FIG. 3 again in another arrangement of the previously discussed components with the addition of external heat removal. For this arrangement, the location of the sulfur adsorbent beds have been moved as compared to the embodiment in FIG. 2. In particular, this biogas cleaning system 333 is the same as FIG. 2 for the biogas stream flow from the inlet biogas stream 31 to the hydrodesulfurization catalyst bed 340, where biogas stream 56 that leaves the hydrodesulfurization catalyst bed 340 enters directly into a bypass valve 595 as shown, whereby typically most or all of the flow is diverted to biogas stream 59 in order to preheat the incoming biogas in recuperative heat exchanger 310. Biogas stream 62 then leaves the heat exchanger 310 to become biogas stream 63, which enters in the sulfur adsorbent bed 605 that operates at or near ambient temperature. Alternative materials that would be suitable to capture hydrogen sulfide at lower temperatures includes activated carbon. Indeed, the use of the upstream hydrodesulfurization catalyst bed to hydrogenate most of the sulfur species to hydrogen sulfide means that the breakthrough capacity of the carbon bed can be increased dramatically, from perhaps 2% sulfur capture by weight up to perhaps 30% sulfur capture by weight in some examples when a slip stream of a small amount of oxygen is added just prior to the carbon bed. This is because hydrogen sulfide is much easier to capture. This is another example of how the hydrodesulfurization catalyst can assist with the economics of the utilization of adsorbents while still providing low sulfur outputs. Biogas stream 64 leaves the sulfur adsorbent bed and enters into the sulfur polisher adsorbent bed 610 to remove the last amounts of sulfur such that in biogas stream 65 there is less than 50 parts per billion of sulfur. The low temperature polisher bed can be of the same type as the high temperature bed, for instance reduced copper on alumina. Though the capacity is somewhat reduced the purity of the biogas out of the polisher increases further as compared to the hot process.

The exception to this typical flow through the heat exchanger 310 of biogas cleaning system 333, is when the exothermic temperature rise in the de-oxidizer catalyst bed is too high and some heat needs to be dumped from the hot loop defined by the hot side of the economizer heat exchanger 310. In this case bypass valve 595 in response to control signal from thermal sensor TE (not numbered) diverts some of the biogas flow through biogas stream 60, which enters into a heat removal component such as air cooled radiator 600 to cool the biogas to close to ambient temperature. Biogas stream 61 then leaves the air cooled radiator 600 and is mixed with biogas stream 62 to become biogas stream 63, which enters in the primary sulfur adsorbent bed or beds that operate at or near ambient temperature in order to remove the bulk of the hydrogen sulfide present in the biogas. The heat removal may alternately be other heat exchangers or liquid cooling systems. Biogas stream 64 leaves the primary sulfur adsorbent bed or beds and enters into the sulfur polisher adsorbent bed to ensure the removal of the last amounts of sulfur such that in biogas stream 65 there is less than 50 parts per billion of sulfur. The biogas cleaning system 333 is well suited for providing biogas fuel of quality for a fuel cell generator.

Figure 3:
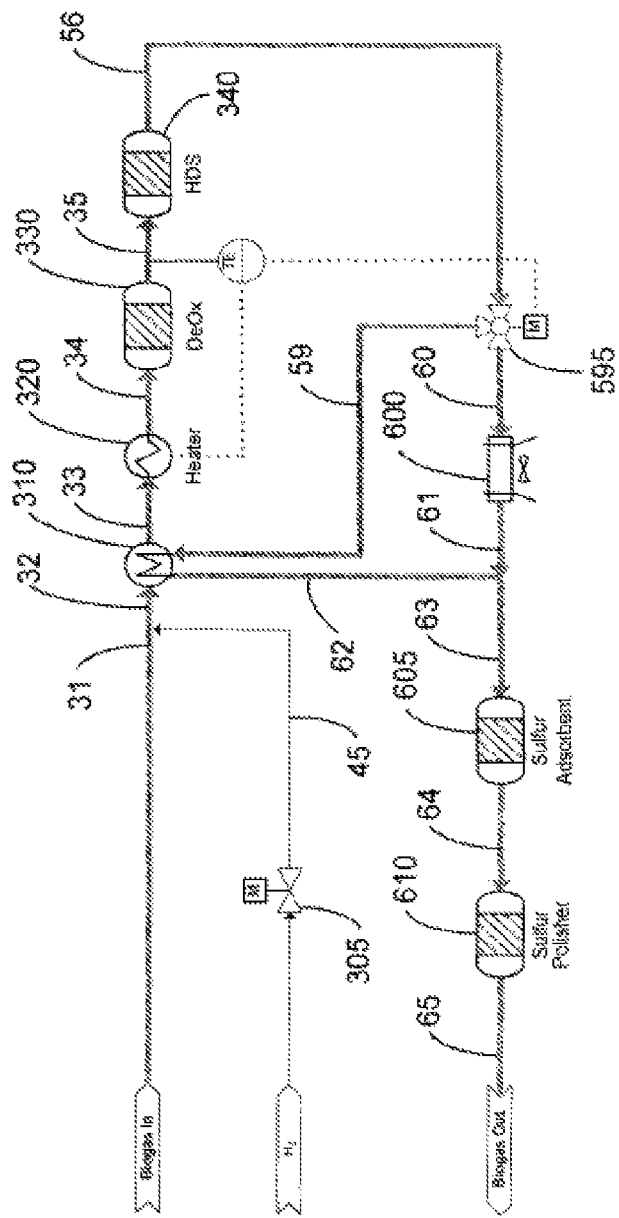
FIG. 3 is a schematic flow diagram illustrating an embodiment of a biogas cleaning system with a heat removal stage with the sulfur adsorbent beds operating at roughly ambient temperature.
Figure 4:
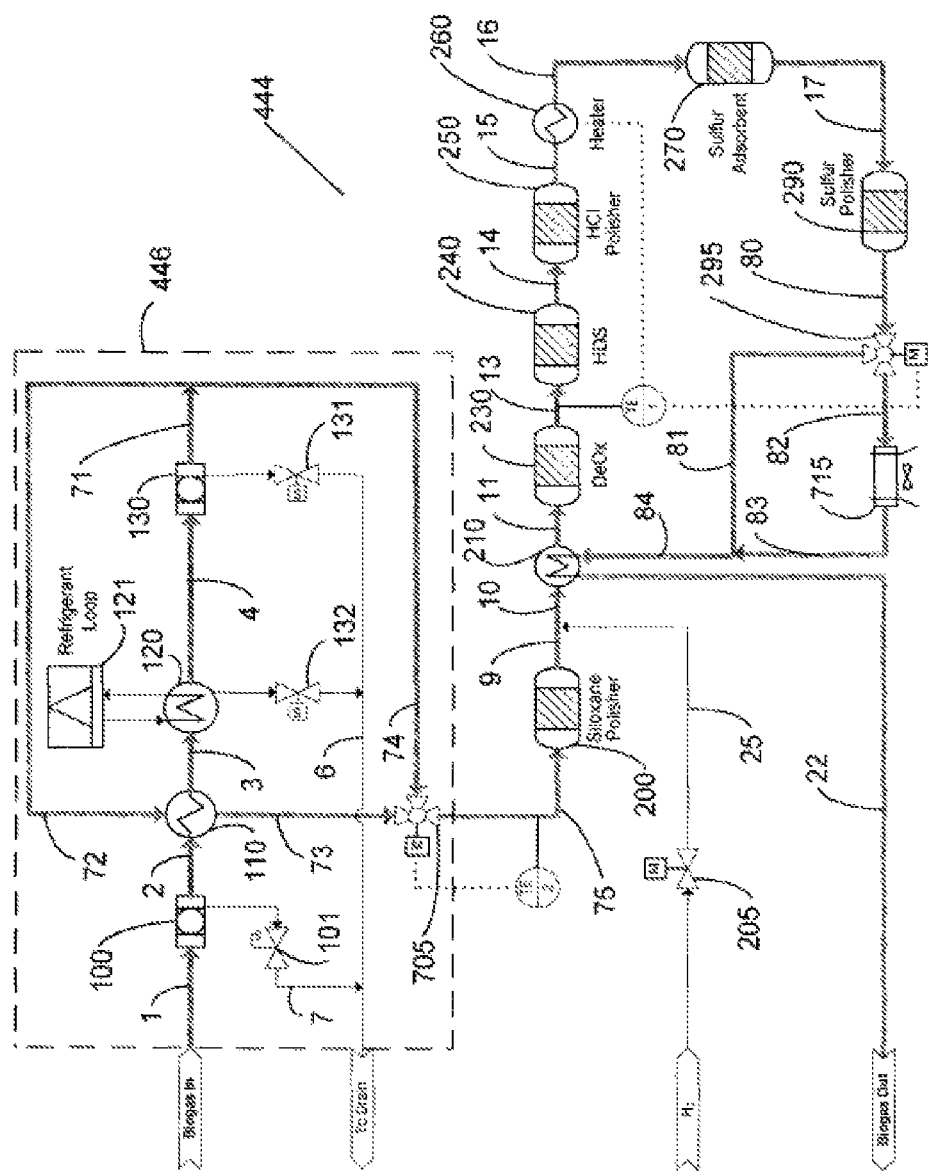
FIG. 4 is a schematic flow diagram illustrating an embodiment of a biogas cleaning system showing integration of a pre-cooling stage, heat removal stage and flow controls for adjusting incoming biogas temperature and biogas temperature following the oxidation combustion (DeOx) stage, with the sulfur adsorbent beds operating at roughly ambient temperature.

The heat removal arrangement of FIG. 3, is applied to the preferred system shown in FIG. 1, as shown in biogas cleaning system 444 in FIG. 4. There are some additional features in the system 444 described as differences to the system 111 of FIG. 1. In contrast for system 444, the cold biogas 71 that leaves separator/filter 130 is split into two as biogas streams 72 and 74. Biogas stream 72 is heated by the economizer heat exchanger 110 and becomes biogas stream 73 at a hotter temperature. The proportion of biogas flow from biogas stream 73 versus the flow from biogas stream 74 is controlled by mixing valve 705 such that the mixed biogas stream 75 out of mixing valve 705 is at a target temperature as measured by thermal sensor TE2. This lower biogas temperature (compared to FIG. 1) means that the downstream economizer heat exchanger 210 can be economically sized smaller but still sufficient to achieve a temperature at biogas stream 22 low enough for use or storage as a biogas fuel in downstream equipment. If there is a necessity to remove more water in biogas stream 22 leaving the system due to combustion of hydrogen within the de-oxidizer bed 230, then it is possible to further cool the gas with the addition of another refrigerant loop heat exchanger (not shown) on biogas stream 22 so that the biogas can be cooled further and the water can be removed. The cooling fluid can come from the same upstream cooling system for this intermittent downstream cooling. The only reason that this may be required is to meet a lower humidify specification for downstream equipment.

Another difference in FIG. 4 is the addition of a heat removal component for additional control of the process in the hot loop of the heat exchanger having the contaminant cleaning components. When the oxygen concentration in the biogas stream 11 is high, for example 2% oxygen, and the combustion of hydrogen in the de-oxidizer bed 230 creates a substantial amount of heat in the hot loop defined by the hot side of heat exchanger 210, then heat needs to be dumped from the hot loop or else it may go out of control causing damage. Another way to dump heat is similar to the heat removal component arranged in FIG. 3, by splitting the heated biogas stream 80 coming from the sulfur polisher 290 such that a portion of this stream as biogas stream 82 goes through an air cooled radiator 715 (or a non insulated pipe or equivalent) bringing down the temperature in a biogas stream 83, which is then mixed with the diverted or bypassed biogas stream 81 such that the temperature of the mixed biogas stream 84 going to the economizer heat exchanger 210 is at a lower temperature. Bypass valve 295 controls this bypassing in response to temperature following the deoxidizer catalyst bed 230 with associated thermal sensor TE 1. This heat removal, in effect, reduces the temperature of biogas stream 11 such that with the larger exothermic temperature rise in de-oxidizer bed 230 and resulting biogas stream 13 is at a target temperature for downstream components as described previously. The biogas cleaning system 444 has the benefits of enhanced control of necessary heating of the biogas stream and contaminant removal components.

Figure 5:
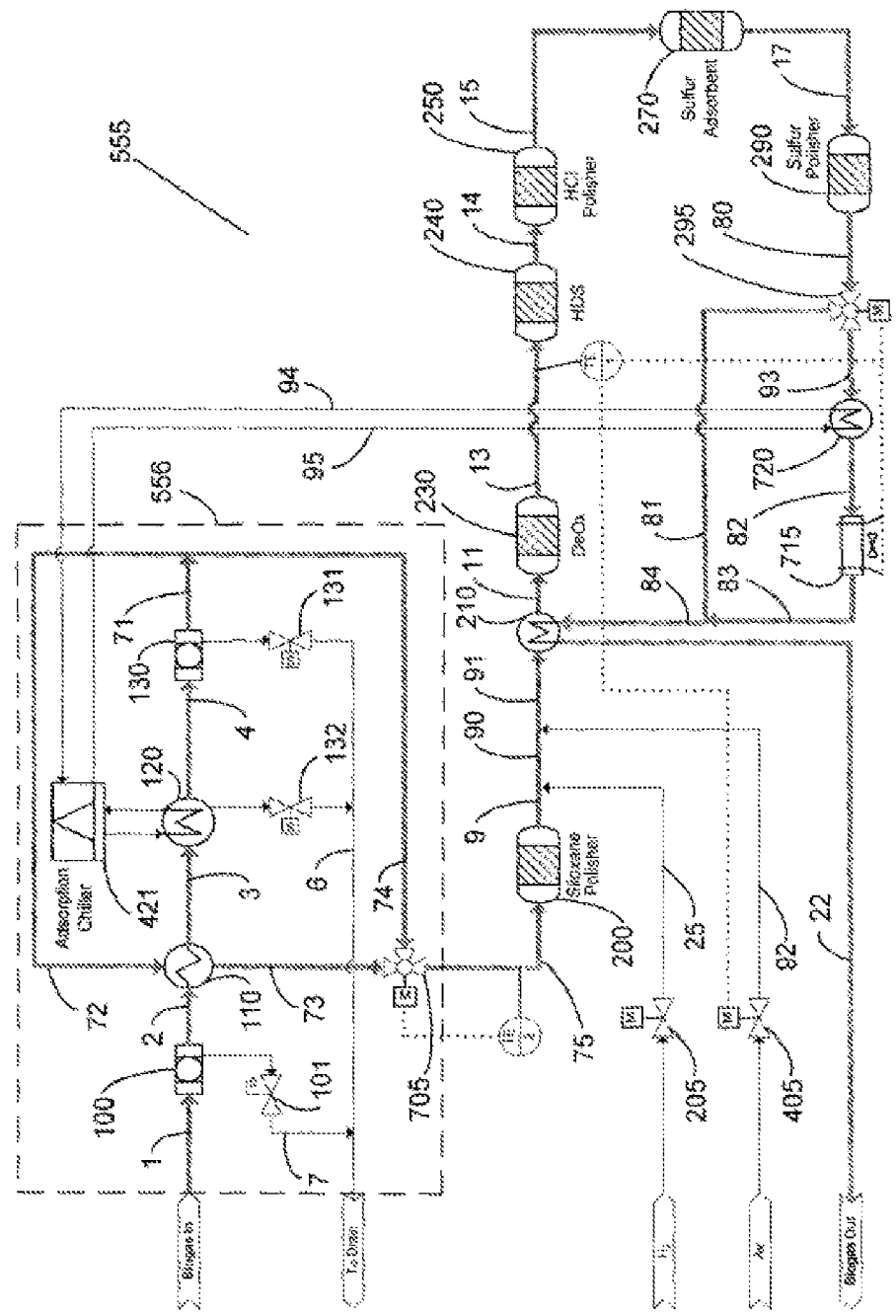
FIG. 5 is a schematic flow diagram illustrating an embodiment of a biogas cleaning system showing integration of a pre-cooling stage, heat removal stage and flow controls for adjusting incoming biogas temperature and biogas temperature following the oxidation combustion (DeOx) stage, showing a modified pre-cooling stage utilizing and recycling waste heat from the biogas cleaning process for improved efficiency.

The initial stage of contaminant removal by condensation, and water removal is described in FIG. 1 as a pre-treatment subsystem. To reduce overall system power requirements through integration, heat removed from downstream processes can be arranged to be used in this upstream subsystem for a net aggregate power efficiency gain that is more economical. Such an integrated efficient arrangement is shown in FIG. 5 as biogas cleaning system 555. In particular, in the case when there is extra heat in the hot loop defined by the hot side of heat exchanger 210, the biogas stream 80 from the hot sulfur polisher 290 is split with valve 295 into biogas streams 81 and 93. Biogas stream 93 then enters into a heat exchanger 720 with a fluid 94 on the other side that can be heated and circulated for use with an adsorption chiller 421 used in the condenser subsystem 556. An adsorption chiller has a heat exchange medium that cools with waste heat [an example is: http:www.energysolutionscentcr.org/resources/PDFs/ GT_W03_Small_Absorption_Chillers.pdf e.g. Yazaki gas fired absorption unit]. The hot adsorption chiller fluid 95 then is flows into the adsorption chiller system 421 that is used to replace the previous electrically driven refrigerant based cooling system. The inlet biogas to system 555 flows through this modified condenser arrangement to knock out water and possibly siloxanes. The recycling of this waste heat is more economical and than the electricity that the electrically driven cooling system would need since the biogas is typically a cheaper resource than electricity. The biogas cleaning system 555 provides benefits of efficiently integrating siloxane removal into a biogas cleaning system, with minimization of required power and direct cost reduction in converting the biogas waste to biogas fuel.

For system 555, there is an additional arrangement that would reduce input power requirements. It would be preferable if the electrical heaters (integrated in the beds of cleaning beds 230,240,250,270,290 but not separately shown) in the hot loop were not utilized to supply the heat for the adsorption chillers in the case when there is insufficient oxygen in the biogas and supplemental heat should be provided. One arrangement to reduce using the integrated heaters (not shown) during normal operation of the system would be to generate waste heat by the combustion of either hydrogen or methane within the de-oxidizer by purposely adding oxygen or air into the biogas in a controlled manner. For this purpose, additional control valve 405, (which also could be a blower or compressor), in response to temperature measured after the deoxidizer catalyst bed at thermal sensor TE1, allows a controlled flow of air stream 92 to be mixed with biogas stream 90 to become biogas stream 91 having additional oxygen content. The amount of air to be added is determined with feedback control of the temperature of biogas stream 13 at TE1, since the exothermic temperature rise in the de-oxidizer bed 230 is proportional to the percentage of oxygen that is in the biogas. In this arrangement, it would be possible to introduce only as much heat as is required into the system, such that the heat removal radiator fan 715 would not need to operate and operating power efficiency is maximized. The addition of oxygen into the biogas can be used as an advantage to reduce the heater duty on any system, not just a system utilizing an absorption chiller.

For each of the biogas systems embodiments, there is an optional embodiment wherein a spray wash of water (not shown) is injected prior to the cooling and condensing subsystem in order to allow more impurities to be absorbed with the water and therefore to reduce the burden on downstream impurity adsorbent beds. In general, the combination of the cooling and condensing subsystem with the hydrodesulfurization subsystem means more impurities can be removed than if the cooling and condensing subsystem were acting alone on the biogas.

In alternate embodiments, the biogas cleaning system can use lower temperature sulfur adsorbent media beds such as activated carbon and copper impregnated on zeolite, as examples. If the price of the adsorbent per gram of sulfur adsorbed is comparable or less with low temperature media as compared to high temperature then low temperature media can be a preferred option, so long as the combination of primary sulfur adsorbent and sulfur polisher adsorbent are able to remove the sulfur to less than 50 parts per billion.

The advantage of using the biogas cleaning system described in the embodiments is that very low levels of impurities such as sulfur, siloxanes, chlorine, and oxygen remain in the biogas after the system so that the biogas fuel product is ready for highly sensitive equipment such as a fuel cell system. While particular elements, embodiments and applications have been shown and described, it is understood, of course, that the scope is not limited thereto since modifications may be made by those skilled in the art without departing from the scope of the present disclosure, particularly in light of the foregoing teachings.

What is claimed is:

1. A biogas cleaning method for purifying a biogas waste stream containing methane, carbon dioxide, nitrogen, hydrogen, oxygen, water and impurities that include sulfur, halides, siloxanes, and volatile organic compounds, to form a combustible clean biogas fuel using a biogas cleaning system, the biogas cleaning system comprising:
 (i) a gas control system operable to blend hydrogen gas into a biogas waste stream, said gas control system having a hydrogen flow controller and a hydrogen port,
 (ii) a deoxidizer catalyst bed fluidly coupled downstream of said gas control system operable to receive and catalytically combust a blended hydrogen gas with oxygen remaining in said biogas waste stream, whereby oxygen is removed from said biogas waste stream and said biogas waste stream is heated, thereby producing a heated biogas stream,
 (iii) a hydrodesulfurization catalyst bed fluidly coupled downstream of said deoxidizer catalyst bed receiving said heated biogas stream, said hydrodesulphurization catalyst bed hydrogenating sulfur species to hydrogen sulfide, and
 (iv) a first hydrogen sulfide removal adsorption bed fluidly coupled downstream of said hydrodesulfurization catalyst bed to remove sulfur from said biogas stream,
 wherein the method for purifying said biogas waste stream comprises:
 (a) using a biogas source to introduce said biogas waste stream into the biogas cleaning system, said biogas source comprising between 50% to 75% methane, between 25% to 50% carbon dioxide, up to 10% nitrogen, up to 1% hydrogen, an amount of sulfur up to 3% and an amount of oxygen up to 2% by volume,
 (b) blending hydrogen with said biogas waste stream using said gas control system,
 (c) combusting said blended hydrogen and said biogas stream in said deoxidizer catalyst bed to remove oxygen and heat said biogas stream to a range of 250° C. to no higher than 400° C.,
 (d) hydrogenating said heated biogas stream in said hydrodesulfurization catalyst bed to convert sulfur species to hydrogen sulfide, and (e) adsorbing said hydrogen sulfide from said biogas stream, whereby said combustible clean biogas fuel is provided.

2. The biogas cleaning method of claim 1, wherein said gas control system provides added hydrogen concentration greater than 2%.

3. The biogas cleaning method of claim 1, wherein said oxygen concentration of said biogas source is between 1.5% to 2% by volume.

4. The biogas cleaning method of claim 1, wherein said biogas cleaning system further comprises:
(vi) a sulfur polisher adsorption bed fluidly coupled downstream of said first hydrogen sulfide removal adsorption bed to remove trace sulfur levels from said biogas stream, said sulfur polisher adsorption bed comprising copper or nickel in a reduced or oxide state; and wherein said method further comprises
(f) adsorbing trace hydrogen sulfide to further remove said hydrogen sulfide from said biogas stream using said sulfur polisher.

5. A biogas cleaning method for purifying a biogas waste stream containing methane, carbon dioxide and water and impurities that may include sulfur, halides, siloxanes, and volatile organic compounds, to form a combustible clean biogas fuel using a biogas cleaning system, the biogas cleaning system comprising:
(i) a gas control system operable to blend hydrogen gas into said biogas waste stream, said gas control system having a hydrogen flow controller and a hydrogen port,
(ii) a deoxidizer catalyst bed fluidly coupled downstream of said gas control system operable to receive and catalytically combust a blended hydrogen gas with any oxygen remaining in said biogas waste stream, whereby any oxygen is removed from said biogas waste stream and said biogas waste stream is heated, thereby producing a heated biogas stream,
(iii) a hydrodesulfurization catalyst bed fluidly coupled downstream of said deoxidizer catalyst bed receiving said heated biogas stream, the hydrodesulphurization catalyst bed hydrogenating any sulfur species to hydrogen sulfide and hydrogenating any chlorine species to hydrogen chloride,
(iv) a first hydrogen sulfide removal adsorption bed fluidly coupled downstream of said hydrodesulfurization catalyst bed to remove sulfur from said biogas stream,
(v) a sulfur polisher adsorption bed fluidly coupled downstream of said first hydrogen sulfide removal adsorption bed to remove any trace sulfur levels from said biogas stream, said sulfur polisher adsorption bed comprising copper or nickel in a reduced or oxide state,
(vi) a chlorine removal adsorbent bed upstream of said first sulfur removal adsorbent bed,
(vii) a siloxane removal adsorption bed for the purpose of removing any siloxanes from the biogas, and
(viii) a biogas precooler fluidly coupled upstream of said hydrogen port,
wherein the method for purifying a biogas waste stream comprises:
(a) using a biogas source to introduce a biogas waste stream into the biogas cleaning system, said biogas source comprising between 50% to 75% methane, between 25% to 50% carbon dioxide, up to 10% nitrogen, up to 1% hydrogen, up to 3% sulfur and up to 2% oxygen by volume,
(b) pre-cooling said biogas waste stream to reduce any volatile organic compounds and water,
(c) absorbing any siloxanes to remove said any siloxanes from said biogas waste stream,
(d) blending hydrogen with said biogas waste stream using said gas control system,
(e) combusting said blended hydrogen with any remaining oxygen in said biogas waste stream in said deoxidizer catalyst bed to remove any remaining oxygen and heat said biogas waste stream to a range of 250° C. to no higher than 400° C.,
(f) hydrogenating said heated biogas stream to convert any sulfur species to hydrogen sulfide and to convert any chlorine species to hydrogen chloride,
(g) adsorbing any hydrogen chloride to remove any said hydrogen chloride from said biogas stream,
(h) adsorbing any hydrogen sulfide in said hydrodesulfurization catalyst bed to remove any said hydrogen sulfide from said biogas stream using sulfur adsorbent bed, and
(i) adsorbing any trace hydrogen sulfide to further remove any said hydrogen sulfide from said biogas stream using said sulfur polisher,
whereby a clean biogas fuel is provided.

6. The biogas cleaning method of claim 5, wherein said biogas precooler is selected from the group consisting of (i) a refrigerant loop providing less than approximately −10° F. to condense water and contaminants, (ii) a refrigerant loop providing between −10° F. and 32° F. to condense water and some contaminants, and (iii) a water condenser operable between 32° F. and 50° F. to condense out water content.

7. The biogas cleaning method of claim 5, wherein said biogas precooler is comprised of a water sprayer and water separator for the purpose of precooling said biogas stream and absorbing some of the impurities comprising at least sulfur dioxide and hydrogen sulfide in the water.

8. The biogas cleaning method of claim 5, wherein said siloxane removal adsorption bed is formed of one selected from the group of activated carbon, silica gel, molecular sieve, or zeolite.

9. The biogas cleaning method of claim 5, wherein said deoxidizer catalyst bed includes a noble metal catalyst selected from the group of platinum, palladium, rhodium, or metals in a reduced state.

10. The biogas cleaning method of claim 5, wherein said hydrodesulfurization catalyst bed includes metals selected from the group of cobalt, molybdenum and nickel.

11. The biogas cleaning method of claim 5, wherein said hydrogen chloride removal adsorption bed comprises in part disodium oxide.

12. The biogas cleaning method of claim 5, wherein said sulfur adsorption bed comprises active compound selected from the group of zinc oxide, iron oxide, and activated carbon.

13. The biogas cleaning method of claim 5, wherein the resulting clean biogas fuel has reduced contaminant concentrations, including sulfur less than 50 ppb, halides less than 50 ppb and siloxanes less than 50 ppb.

14. The biogas cleaning method of claim 5, wherein the biogas cleaning system further comprises:
(ix) a plurality of sulfur adsorbent beds arranged in a lead and lag arrangement such that during operation of one of the plurality of sulfur adsorbent beds is removed from said biogas stream offline and changed while at least one other adsorbent bed is operable inline to said biogas stream.

15. The biogas cleaning method of claim 5, wherein said oxygen composition of the biogas source is between 1.5% to 2% by volume.

\* \* \* \* \*